US011633360B2

(12) United States Patent
Lee et al.

(10) Patent No.: US 11,633,360 B2
(45) Date of Patent: Apr. 25, 2023

(54) METHOD FOR PREPARING BIODEGRADABLE MICROSPHERES USING STABILIZED SINGLE-PHASE MIXED SOLUTION

(71) Applicant: HLB PHARMACEUTICAL CO., LTD, Namyangju-si (KR)

(72) Inventors: Sang Hwi Lee, Suwon-Si (KR); Mijung Kim, Busan (KR); Dooyong Jeong, Suwon-Si (KR); Mi Jung Kim, Namyangju-Si (KR); Wan Joo Kim, Seoul (KR); So Kyoung Joo, Seongnam-Si (KR)

(73) Assignee: HLB PHARMACEUTICAL CO., LTD, Namyangju-si (KR)

( * ) Notice: Subject to any disclaimer, the term of this patent is extended or adjusted under 35 U.S.C. 154(b) by 383 days.

(21) Appl. No.: 17/049,942

(22) PCT Filed: Apr. 22, 2019

(86) PCT No.: PCT/KR2019/004800
§ 371 (c)(1),
(2) Date: Oct. 22, 2020

(87) PCT Pub. No.: WO2019/208982
PCT Pub. Date: Oct. 31, 2019

(65) Prior Publication Data
US 2021/0093572 A1 Apr. 1, 2021

(30) Foreign Application Priority Data
Apr. 23, 2018 (KR) ........................ 10-2018-0046523

(51) Int. Cl.
*A61K 38/08* (2019.01)
*A61K 9/14* (2006.01)
*A61K 9/16* (2006.01)
*A61K 38/09* (2006.01)

(52) U.S. Cl.
CPC .......... *A61K 9/1682* (2013.01); *A61K 9/1647* (2013.01); *A61K 38/08* (2013.01); *A61K 38/09* (2013.01)

(58) Field of Classification Search
None
See application file for complete search history.

(56) References Cited

U.S. PATENT DOCUMENTS

2010/0028454 A1 2/2010 Kim
2010/0189800 A1* 7/2010 Markland ............ A61K 9/1647
264/4.1
2015/0080322 A1* 3/2015 Futo ........................ A61P 15/16
514/21.6
2017/0020823 A1 1/2017 Kim et al.
2017/0216210 A1 8/2017 Suh et al.
2017/0281547 A1* 10/2017 Karavas ............... A61K 9/0019

FOREIGN PATENT DOCUMENTS

| CN | 106038492 A | 10/2016 |
|---|---|---|
| KR | 10-2009-0029339 A | 3/2009 |
| KR | 10-2010-0101190 A | 9/2010 |
| KR | 101 039 237 B1 | 6/2011 |
| KR | 10-1558083 B1 | 10/2015 |
| KR | 10-2016-0019020 A | 2/2016 |
| KR | 10-1663560 B1 | 9/2016 |
| KR | 10-1936040 B1 | 1/2019 |
| WO | 2004/045633 A2 | 6/2004 |
| WO | 2008/075762 A1 | 6/2008 |

OTHER PUBLICATIONS

European Patent Office; European Search Report received in EP Application No. 19793561.2; dated Apr. 7, 2022; 7 pages.
Hiroaki et al.; "Drug delivery using biodegradable microspheres;" Journal of Controlled Release, Elsevier, Amsterdam, NL; vol. 28, No. 1-3; Jan. 1, 1994; pp. 121-129.
Luan et al.; "Key parameters affecting the initial release (burst) and encapsulation efficiency of peptide-containing poly(lacride-co-glycolide) microparticles;" International Journal of Pharmaceutics, Elsevier, NL; vol. 324, No. 2; Nov. 6, 2006; pp. 168-175.
Hirota, K. et al., "Characterizing release mechanisms of leuprolide acetate-loaded PLGA microspheres for IVIVC development I: In vitro evaluation," Journal of Controlled Release, 2016, vol. 244, pp. 302-313, 12 pages.
Office Action issued in Korean patent application No. 10-2018-0046523 dated Jul. 4, 2018, 5 pages.
International Search Report for International Application No. PCT/KR2019/004800, dated Jul. 24, 2019, 5 pages.

* cited by examiner

*Primary Examiner* — Kevin S Orwig
(74) *Attorney, Agent, or Firm* — Insight Law Group, PLLC; Seung Lee

(57) ABSTRACT

The present invention relates to a method for preparing biodegradable microspheres using a single-phase mixed solution containing water, alcohol, and dichloromethane. Provided is a method for preparing a biodegradable microsphere having a uniform drug loading efficiency by preparing and using a single-phase mixed solution in which no phase separation occurs without using a thickener and a surfactant. The preparation method of the present invention has the feature of keeping the content of a loaded drug uniform until a final biodegradable microsphere is prepared, by using a single-phase mixed solution in which no phase separation by a solvent occurs in the preparation process. Thus, the preparation method of the present invention is remarkably useful for the preparation of biodegradable microspheres.

7 Claims, 5 Drawing Sheets

Example 3

Example 4

METHOD FOR PREPARING BIODEGRADABLE MICROSPHERES USING STABILIZED SINGLE-PHASE MIXED SOLUTION

CROSS REFERENCE TO RELATED APPLICATIONS

This application is a U.S. National Entry and claims priority to PCT International Patent Application No. PCT/KR2019/004800, filed Apr. 22, 2019, and entitled "METHOD FOR PREPARING BIODEGRADABLE MICROSPHERES USING STABILIZED SINGLE-PHASE MIXED SOLUTION," which claims priority to the Republic of Korean Patent Application No. 10-2018-0046523 filed Apr. 23, 2018, the entire disclosures of which are incorporated herein by this reference.

TECHNICAL FIELD

The present invention relates to a method of preparing biodegradable microspheres using a single-phase mixed solution containing water, alcohol, and dichloromethane, and more particularly, to a method of preparing biodegradable microspheres having uniform drug loading efficiency by preparing and using a single-phase mixed solution in which phase separation does not occur even though a thickener and a surfactant are not used.

BACKGROUND

Biodegradable microspheres have been researched as carriers for delivering drugs into the body. The in-vivo elimination rates of the biodegradable microspheres are determined by degradation mechanisms and degradation rates of biodegradable polymers, which are main components, and depending on the in-vivo elimination rates of the polymers, it takes one week to six months for encapsulated drugs to be released.

The biodegradable microspheres may be a single-emulsion type, such as O/W (oil in water), W/O (water in oil), O/O (oil in oil), S/O (solid in oil), S/W (solid in water), or the like, or a double-emulsion type, such as W/O/W (water/oil/water), O/W/O (oil/water/oil), or S/O/W (solid/oil/water). Among these, the most widely used emulsion types for industrial use are O/W single emulsions and W/O/W double emulsions.

Among the methods for preparing biodegradable microspheres, the most widely known and used method is a solvent evaporation method, which includes the steps of evaporating an organic solvent used for preparing microspheres and hardening the microspheres. Other methods such as spray drying and ultrasonic method have been researched for preparing the biodegradable microspheres, but the spray-drying method has a disadvantage in that types of solvents that can be used are limited, and the sonication-induced crushing method has a disadvantage in that loaded drugs are directly exposed to ultrasonic energy.

When biodegradable microspheres are prepared by the solvent evaporation method, in the case of an O/W (single emulsion)-type, a water-immiscible non-polar organic solvent is used as an internal oil phase, and the O/W-type microspheres may be prepared by simultaneously dissolving a biodegradable polymer and a drug in the non-polar organic solvent and quickly dispersing the resultant in an aqueous phase in which a surfactant is dissolved. However, this method can only be used when a drug to be loaded is soluble in a non-polar solvent, and there is a limitation in loading drugs insoluble in non-polar solvents in the biodegradable microspheres.

For a drug soluble in polar solvents (water-soluble drugs), W/O/W (double emulsion)-type microspheres are mainly used, and the W/O/W-type microspheres may be obtained by preparing a W/O emulsion by dissolving the water-soluble drug in a primary aqueous phase and vigorously stirring the same in a non-polar soluble solvent in which a polymer is dissolved, and then quickly dispersing the W/O emulsion in a secondary aqueous phase in which a surfactant is dissolved. However, in this case, economical efficiency is very low in that since the W/O emulsion is prematurely phase-separated into the non-polar organic solvent and the aqueous solution during the preparation of microspheres proceeds (i.e., production of a batch proceeds), it becomes more difficult to obtain biodegradable microspheres having uniform loading efficiency of water-soluble drugs, and since the uniformity of drug loading efficiency of microspheres prepared toward the end of the preparation process is remarkably low, formulation specifications are not met, and thus the microspheres are discarded.

As one way to improve the uniformity of drug loading efficiency in the preparation of W/O/W-type microspheres using a W/O emulsion, research has been conducted to improve the colloidal stability of the W/O emulsion. For example, in Korean Patent No. 10-1558083, colloidal stability was improved by increasing the viscosity of a W/O emulsion using a thickener, and in Korean Patent No. 10-1663560, the dispersion of a water-soluble drug was promoted using a surfactant. However, biodegradable microspheres prepared by such conventional preparation methods have disadvantages in that the thickener or surfactant remains inside the prepared microspheres, making it difficult to identify the amounts of the remaining thickener or surfactant.

Therefore, for the preparation of biodegradable microspheres having uniform drug loading efficiency, there has been a need to develop a method of preparing microspheres in which microspheres obtained in early preparation stages (early batches) and later preparation stages (later batches) have uniform drug loading efficiency even though a thickener and a surfactant are not used so that a uniform microsphere formulation is prepared.

SUMMARY

Hence, as a result of performing continued research to meet the requirements of the related art, the inventors of the present invention have found that when a mixed solution containing water, alcohol, and dichloromethane in a specific mixing ratio was used, the solvents surprisingly did not phase-separate, and thus confirmed that it is possible to simultaneously dissolve a drug and a biodegradable polymer and prepare biodegradable microspheres having uniform drug loading efficiency, and thereby completed the present invention.

Therefore, the present invention is directed to providing a method of preparing biodegradable microspheres having uniform drug loading efficiency using a single-phase mixed solution containing water, alcohol, and dichloromethane.

In addition, the present invention is directed to providing biodegradable microspheres having uniform drug loading efficiency, which are prepared by the above preparation method.

In addition, the present invention is directed to providing a method of preparing a single-phase mixed solution for preparing biodegradable microspheres, in which phase separation does not occur even though a thickener and a surfactant are not used.

DETAILED DESCRIPTION

One aspect of the present invention provides a method of preparing biodegradable microspheres, which includes the following steps:

i) dissolving a drug in a mixed solvent in which water and alcohol are mixed in a volume ratio of 1:4 to 1:9;

ii) adding a drug solution obtained in the step i) to a non-polar organic solvent in which a biodegradable polymer is dissolved, and thus forming a single-phase mixed solution;

iii) dispersing the single-phase mixed solution in an aqueous phase in which a surfactant is dissolved, and thus forming a microsphere emulsion;

iv) evaporating the non-polar organic solvent in the microsphere emulsion formed in the step iii), and then hardening the microspheres; and v) obtain the microsphere powder by a freeze-dryings Hereinafter, each step of the method of preparing biodegradable microspheres of the present invention will be described in detail.

Step i): Dissolution of Drug in Mixed Solvent

A drug is dissolved in a mixed solvent in which water and alcohol are mixed in a volume ratio of 1:4 to 1:9.

The "drug" in the preparation method of the present invention is not limited as long as it is a pharmaceutically acceptable water-soluble drug, but the drug is preferably a water-soluble drug, a biological agent such as a peptide, a protein, an antibody, a nucleic acid, a cell, or a gene, a bioactive substance such as a hormone or a hormone analogue, or a combination thereof and most preferably a peptide.

Examples of peptides in the present invention include leuprorelin, goserelin, triptorelin, buserelin, nafarelin, cetrorelix, argitide, octreotide, and salts thereof.

The "alcohol" in the present invention may be a C1-C3 lower alcohol, preferably methanol, ethanol, propanol, isopropanol, or a combination thereof, and most preferably ethanol.

In a mixture of water and alcohol used as a solvent for dissolving the drug in the present invention, water and alcohol are preferably mixed in a volume ratio of 1:4 to 1:9. When the mixing ratio of water and alcohol is out of the above range, a mixed solution formed in a subsequent step is not stabilized, and thus phase separation (formation of separate solvent layers due to a difference in solvent density) occurs.

The usage amount of the mixed solvent is not particularly limited as long as it is an amount capable of dissolving the drug, but the mixed solvent is preferably used at 1 part by weight relative to 0.05 to 1 part by weight of the drug.

Step ii): Formation of Single-Phase Mixed Solution

The drug solution obtained in the step i) is mixed with a non-polar organic solvent in which a biodegradable polymer is dissolved, and thus a single-phase mixed solution is formed.

In the present invention, the biodegradable polymer forms outer walls of microspheres and is eliminated from the body within a specific period of time, and as the biodegradable polymer, any polymer which is pharmaceutically acceptable and completely soluble in a non-polar organic solvent may be used, and most preferably, poly(lactic-co-glycolic acid), poly(lactic acid), polycaprolactone, which are biodegradable polymers whose units (monomers) are connected by ester bonds, or a combination thereof are used.

In the present invention, a weight-average molecular weight (MW) of the biodegradable polymer is not particularly limited and may be 5,000 to 100,000 g/mol.

In the present invention, the biodegradable polymer may have an intrinsic viscosity of 0.16 to 0.74 dL/g. In the present invention, when the biodegradable polymer has an intrinsic viscosity of less than 0.16 dL/g, the polymer decomposes too quickly, so a drug may not be continuously released for the desired time, and when the biodegradable polymer has an intrinsic viscosity of more than 0.74 dL/g, the polymer decomposes too slowly, so a small amount of a drug may be released, resulting in no medicinal effect.

In the present invention, as the non-polar organic solvent, a solvent which has a higher density than water and a solubility in water of less than 10 wt % so that when mixed only with water, phase separation can be observed with the naked eye may be used, preferably, dichloromethane or chloroform is used, and most preferably, dichloromethane is used.

The usage amount of the non-polar solvent is not particularly limited as long as it is an amount capable of dissolving the biodegradable polymer, but is preferably 1 to 20 times the weight of the biodegradable polymer.

The mixing volume ratio of the drug solution and the non-polar organic solvent in which the biodegradable polymer is dissolved may be in a range in which phase separation does not occur, and is preferably in the range of 1:1 to 1:12 and most preferably in the range of 1:1 to 1:6.

In a single-phase mixed solution formed in this step, phase separation (formation of separate layers due to a difference in solvent density) does not occur (FIG. 1).

It is predicted that the mechanism behind the above result arises from the fact that when a 1:4 to 1:9 (v/v) mixture of water and alcohol is used as a solvent for the drug, the alcohol forms hydrogen bonds with the water, and at the same time, when the drug solution is mixed with the non-polar solvent at a volume ratio of 1:1 to 1:12, the non-polar solvent forms hydrophobic interactions with carbon chains of the alcohol, thus preventing water molecules from being separated from the non-polar solvent.

Step iii): Formation of Microsphere Emulsion

The single-phase mixed solution obtained in the step ii) is dispersed in an aqueous phase in which a surfactant is dissolved, and thus a microsphere emulsion containing the drug is formed.

As the surfactant used in this step of the present invention, any type of surfactant capable of stabilizing the dispersion of the microspheres may be used without limitation, but preferably, Polysorbate 20, Polysorbate 60, Polysorbate 80, polyvinyl alcohol, or a combination thereof is used, and most preferably, polyvinyl alcohol is used.

The surfactant may be dissolved and used in a concentration capable of stabilizing the microsphere dispersion, and is preferably dissolved and used in a concentration of 0.1 to 5% (w/v).

Step iv): Evaporation of Non-Polar Organic Solvent and Hardening the Microspheres The non-polar organic solvent in the microsphere emulsion is evaporated, and then the hardened microspheres are obtained This step may be carried out using a method generally used for evaporating a non-polar organic solvent in a microsphere emulsion and hardening the remainder, such as a stirring method, a heating method, a stirring under reduced pressure method, or a vacuum evaporation method. For example, in this step, the non-polar organic solvent may be evaporated by a heating method in which 30 to 40° C. heat is applied for one to six hours, and the remainder may be hardened.

v) Drying the Suspension to Obtain the Microsphere Powder

The hardened microspheres obtained in the step iv) are freeze-dried, and thus biodegradable microsphere powder is obtained.

The freeze-drying may be carried out by a conventional method. Preferably, to the microspheres suspended in an appropriate solution such as injectable water, an excipient, a dispersant, and the like are added, and subsequently, the microspheres are freeze-dried.

When necessary, the hardened microspheres may be filtered using a sieve before freeze-drying.

According to the preparation method of the present invention, since a drug loading amount is uniformly maintained from an initial stage to later stages of preparation, biodegradable microspheres having uniform drug loading efficiency can be obtained throughout the preparation process.

The biodegradable microspheres prepared by the preparation method of the present invention have a particle size falling within a pharmaceutically acceptable range for injections and preferably has a d50 of 1 to 300 μm (FIG. 3).

In addition, the biodegradable microspheres prepared by the preparation method of the present invention are capable of slowly releasing a drug uniformly loaded inside the microspheres (FIG. 5).

Another aspect of the present invention provides biodegradable microspheres having uniform drug loading efficiency, which are prepared by the above-described preparation method.

The biodegradable microspheres of the present invention are usable as a sustained-release carrier by encapsulating a water-soluble drug.

Still another aspect of the present invention provides a method of preparing a single-phase mixed solution for preparing biodegradable microspheres which is stable and does not undergo phase separation even though a thickener and a surfactant are not used. The preparation method includes the following steps:

a) dissolving a drug in a mixed solvent in which water and alcohol are mixed in a volume ratio of 1:4 to 1:9; and b) adding a drug solution obtained in the step a) to a non-polar organic solvent in which a biodegradable polymer is dissolved, and thus forming a single-phase mixed solution.

In the description of the steps a) and b), the alcohol, volume (mixing) ratio, mixed solvent, drug, biodegradable polymer, non-polar organic solvent, single-phase mixed solution, and the like are the same as defined and described in the steps i) and ii).

The single-phase mixed solution prepared by the preparation method of the present invention is stable and does not undergo phase separation, and thus is highly useful for preparing biodegradable microspheres (FIG. 1). The method of preparing biodegradable microspheres using the single-phase mixed solution of the present invention enables a drug to be evenly distributed inside microspheres, reduces the loss of the drug, and efficiently and economically produces a sustained-release formulation.

Advantageous Effects

A single-phase mixed solution of the present invention is stably maintained from the beginning to the end of preparation since no phase separation occurs, and thus is useful for preparing biodegradable microspheres having uniform loading efficiency throughout the preparation process (i.e., preparation of multiple batches).

Since a drug is evenly distributed in the biodegradable microspheres prepared by the preparation method of the present invention, the drug can be uniformly released in a sustained manner According to the preparation method of the present invention, since a single-phase mixed solution which is stable and does not undergo phase separation by solvents is used in the preparation process, biodegradable microspheres having uniform drug loading efficiency can be prepared with remarkably high efficiency throughout the preparation process.

EMBODIMENTS OF THE INVENTION

Hereinafter, the present invention will be described in more detail through Examples. However, Preparation Examples and Examples are merely illustrative of the present invention, and it will be apparent to those of ordinary skill in the art that the scope of the present invention is not limited to Examples.

PREPARATION EXAMPLE 1: PREPARATION OF SINGLE-PHASE MIXED SOLUTION

Example 1

0.28 g of leuprorelin acetate (polypeptide) was added to a mixture of 0.14 mL of water (injectable water) and 1.0 mL of ethanol, stirred, and completely dissolved, and the solution was added to 3.11 mL of dichloromethane (Daejung Chemicals & Metals Co., Ltd.) in which 1.72 g of poly(D, L-lactic-co-glycolic acid) (Evonik, RG 653 H, Select 5050 DLG 2A) was dissolved and vortexed, and thereby a single-phase mixed solution was obtained.

Example 2

A single-phase mixed solution was prepared in the same manner as in Example 1 except that poly(D,L-lactic acid) (Evonik, R 202 H) was used as a biodegradable polymer instead of poly(D,L-lactic-co-glycolic acid).

Comparative Example 1

A W/O emulsion was prepared by completely dissolving 0.28 g of leuprorelin acetate (polypeptide) in 1.14 mL of water (injectable water) and then adding the solution to 3.11 mL of dichloromethane (Daejung Chemicals & Metals Co., Ltd.) in which 1.72 g of poly(D,L-lactic-co-glycolic acid) (Evonik, RG 653 H, Select 5050 DLG 2A) was dissolved and vortexing.

PREPARATION EXAMPLE 2: PREPARATION OF BIODEGRADABLE MICROSPHERES

Example 3

All of the single-phase mixed solution of Example 1 was injected into 500 mL of a 0.7 wt % aqueous polyvinyl alcohol (PVA) solution at a rate of 0.36 mL/min using a syringe pump while performing homogenization at 7,000 rpm using a homogenizer, and thereby a microsphere emulsion was formed. The formed microsphere emulsion was stirred at 36° C. and 500 rpm for two hours using a mechanical stirrer to evaporate dichloromethane, and the remainder was hardened at 25° C. for 30 minutes. Subsequently, hardened microspheres were filtered using a 75 μm sieve and a 5 μm sieve and then freeze-dried for 48 hours, and thereby biodegradable microsphere powders were obtained.

Example 4

Biodegradable microspheres were obtained in the same manner as in Example 3 except that the single-phase mixed solution of Example 2 was used.

Comparative Example 2

W/O/W-type biodegradable microspheres were obtained in the same manner as in Example 3 except that the W/O emulsion of Comparative Example 1 was used.

Test Example 1: Determination of Occurrence of Phase Separation

Figure 1:
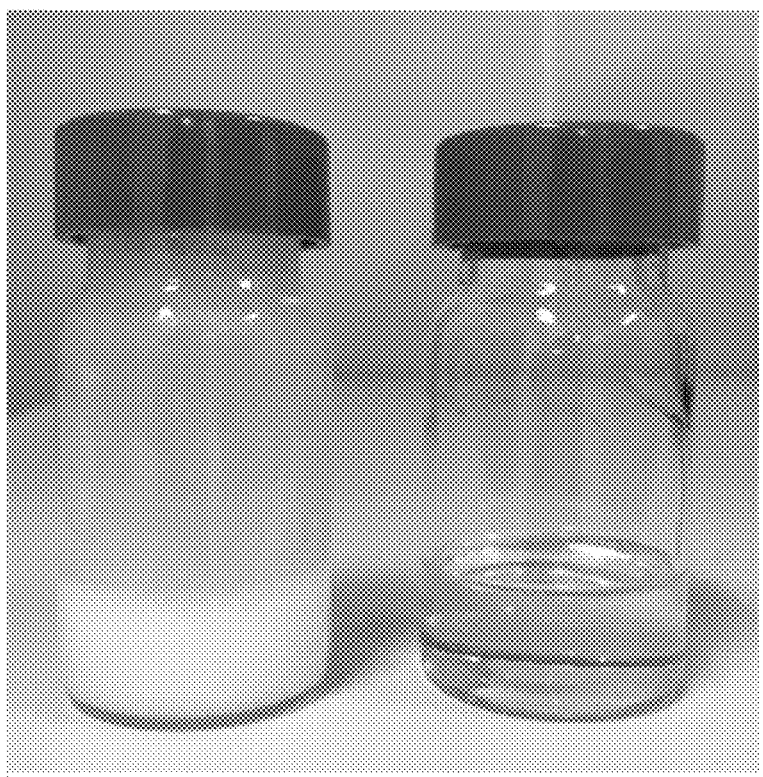
FIG. 1 is a photograph showing whether phase separation occurred in a single-phase mixed solution of the present invention (Example 1) and a conventional W/O emulsion (Comparative Example 1).

The single-phase mixed solution of Example 1 and the W/O emulsion of Comparative Example 1, which were prepared in Preparation Example 1, were visually examined and compared to determine whether phase separation had occurred, and results thereof are shown in the photograph of FIG. 1.

As shown in FIG. 1, it can be seen that in the case of the W/O emulsion of Comparative Example 1, since an interface is generated between the two solutions and phase separation occurred, the W/O layer was present in the form of microdroplets, and thus the W/O emulsion was formed as an opaque solution, but in the case of the single-phase mixed solution of Example 1, since an interface was not generated and phase separation did not occur, the single-phase mixed solution was formed as a transparent solution.

Test Example 2: Analysis of Phase Separation Over Time

Figure 2:
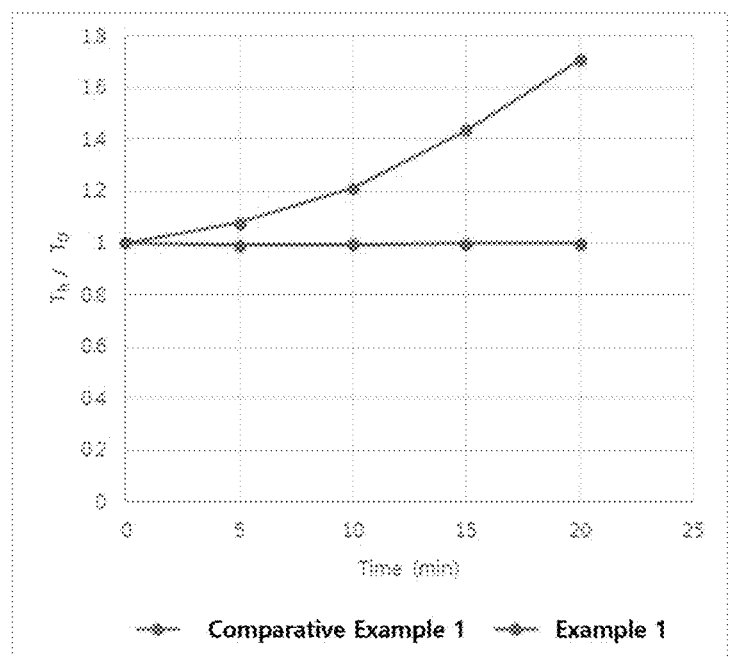
FIG. 2 is a graph showing the results of analyzing whether phase separation occurred over time in a single-phase mixed solution of the present invention (Example 1) and a conventional W/O emulsion (Comparative Example 1).

Each of the single-phase mixed solution of Example 1 and the W/O emulsion of Comparative Example 1, which were prepared in Preparation Example 1, was input in a glass vial, and a change in transmittance over time at room temperature was determined through measurement with a spectrophotometer and using the following equation, and thereby the occurrence of phase separation was analyzed, and results thereof are shown in FIG. 2:

Change in transmittance=$T_h/T_0$ $T_0$: Transmittance measured immediately after preparation of Example 1 or Comparative Example 1

$T_h$: Transmittance measured at time (h) after preparation of Example 1 or Comparative Example 1

As shown in FIG. 2, unlike in the case of the W/O emulsion of Comparative Example 1 in which $T_h$ was gradually increased compared to $T_0$ as water was phase-separated from the emulsion over time and moved to an upper layer portion due to a difference in density, in the case of the single-phase mixed solution of Example 1, transmittance of the solution did not change over time because a phase separation phenomenon did not occur.

Test Example 3: Confirmation of Shapes of Biodegradable Microspheres

Figure 3:
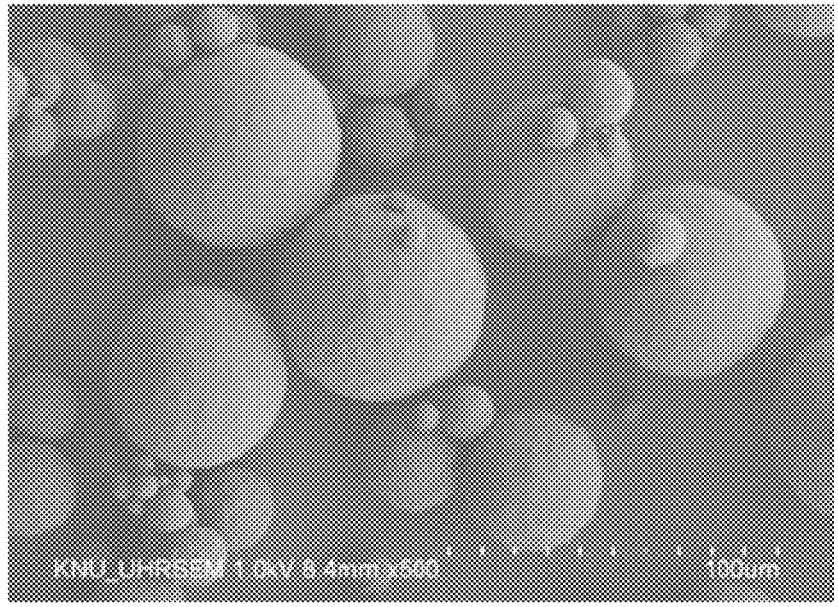
FIG. 3 shows scanning electron microscope images showing the shapes of biodegradable microspheres prepared by a preparation method of the present invention.
Figure 3:
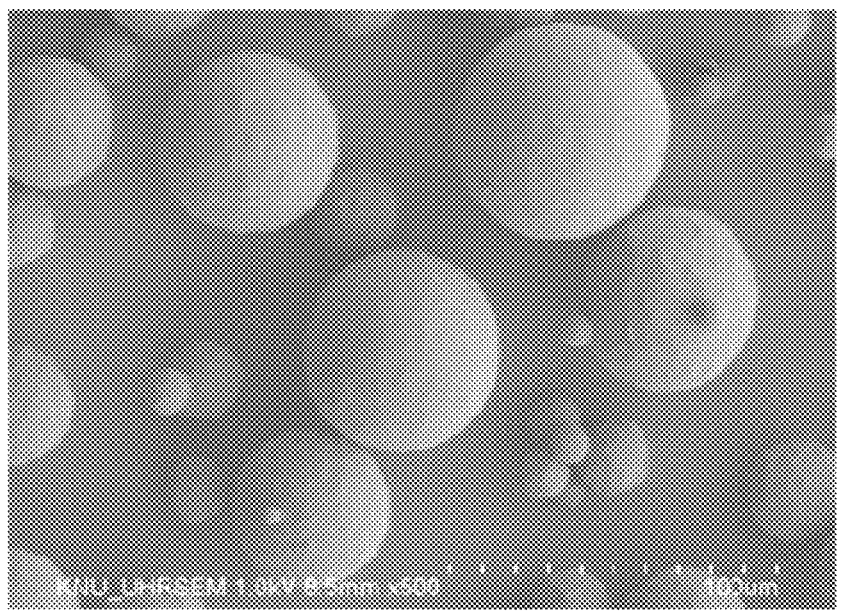

The biodegradable microspheres of Examples 3 and 4, which were prepared in Preparation Example 2, were photographed with an SEM to examine shapes thereof, and the images are shown in FIG. 3.

As shown in FIG. 3, the biodegradable microspheres prepared according to a preparation method of the present invention had particle sizes falling within a pharmaceutically acceptable range for injections, and it can be seen that such biodegradable microspheres were obtainable using various types of biodegradable polymers.

Test Example 4: Measurement of Change in Drug Loading Efficiency of Biodegradable Microspheres Degrees of change in the leuprorelin loading efficiency of the biodegradable microspheres of Example 3 and Comparative Example 2, which were prepared in Preparation Example 2, according to the time elapsed after the microspheres had been prepared were calculated by the following equation, and results thereof are shown in FIG. 4.

Degree of change in loading efficiency (%)=$EE_h/EE_0 \times 100$ $EE_h$: Drug loading efficiency at h minutes after microsphere preparation $EE_0$: Drug loading efficiency immediately after microsphere preparation Drug loading efficiency (%)=Actual drug loading amount per gram of microspheres/Amount of drug added during preparation per gram of microspheres×100

Figure 4:
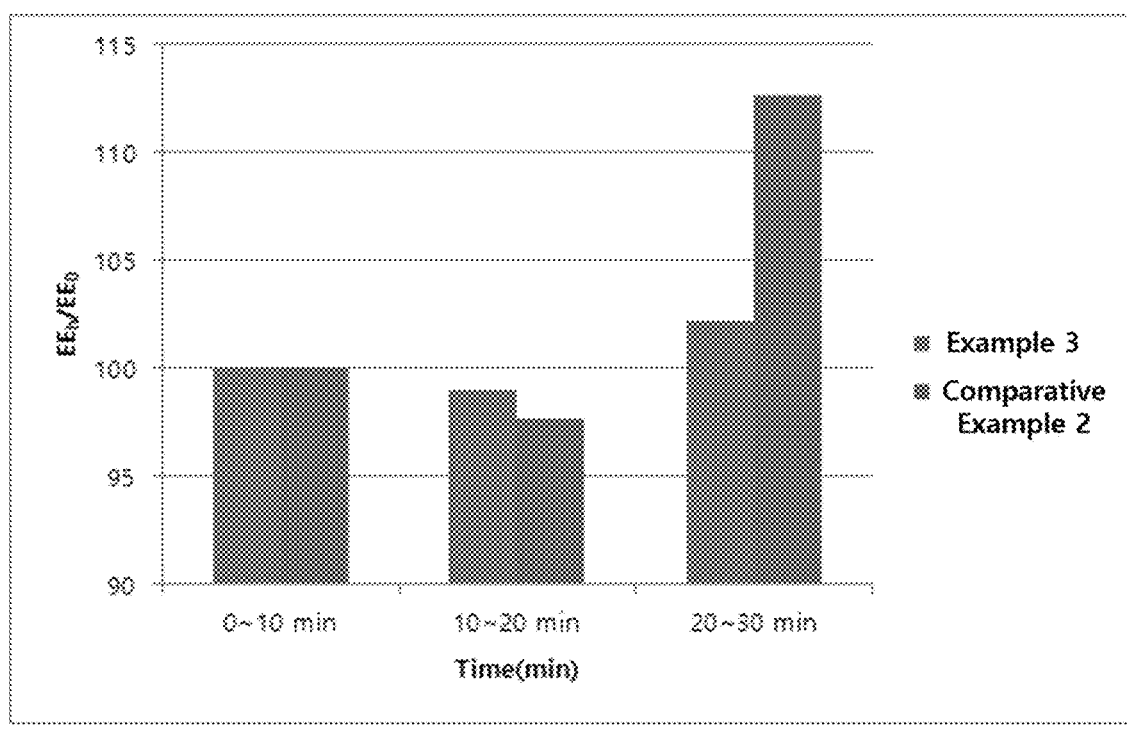
FIG. 4 is a graph for comparing changes in drug loading efficiency of biodegradable microspheres prepared by a preparation method of the present invention (Example 3) and W/O/W-type biodegradable microspheres prepared by a conventional method (Comparative Example 2).

As shown in FIG. 4, it can be seen that unlike the case of the W/O/W-type biodegradable microspheres of Comparative Example 2 where drug loading efficiency greatly changed over time, in the case of the biodegradable microspheres of Example 3, drug loading efficiency was uniform and hardly changed over time.

Test Example 5: Analysis of Drug Release of Biodegradable Microspheres 100 mg of the biodegradable microspheres of Example 4 prepared in Preparation Example 2 was taken and added to 100 mL of a 0.02% aqueous Polysorbate 80 solution, and an accelerated drug release test was carried out while shaking the microspheres at 50±0.5° C. and 125 rpm.

Figure 5:
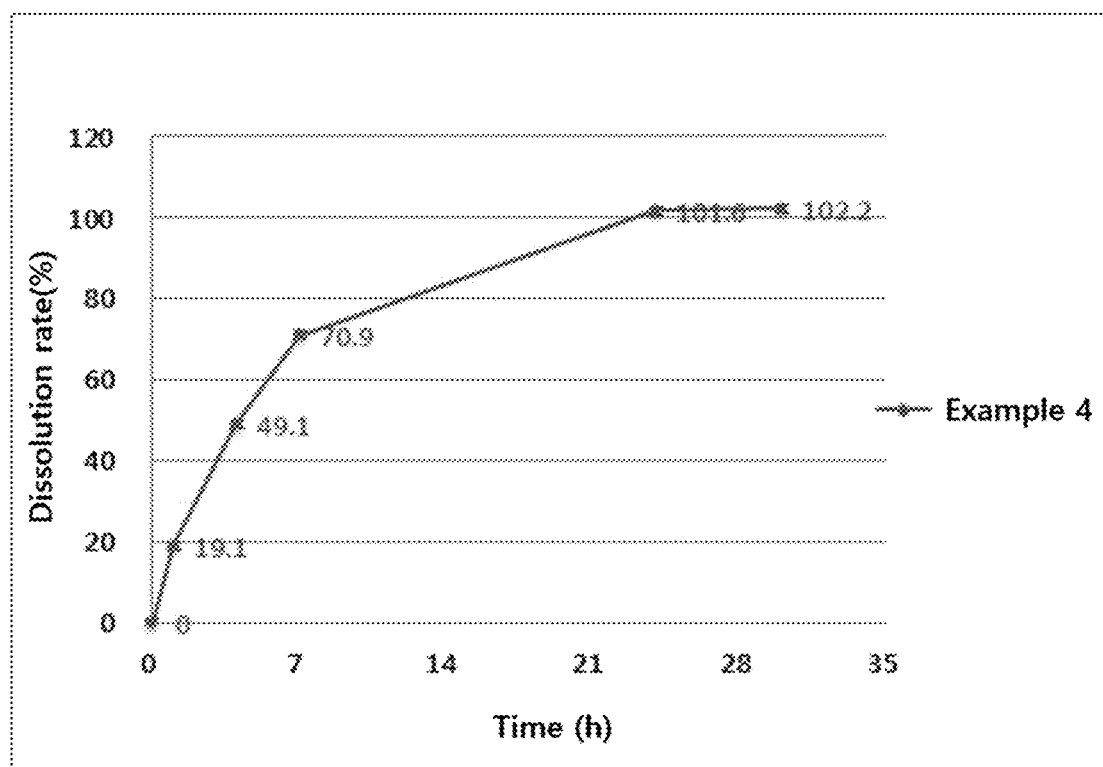
FIG. 5 is a graph showing the results of testing an accelerated drug release rate of biodegradable microspheres prepared by a preparation method of the present invention.

In order to evaluate the release of the drug, 1 mL of an eluate was taken at 1, 4, 7, 24, and 30 hours, followed by measurement of absorbance at 280 nm using a spectrophotometer and calculation of a release rate, and results thereof are shown in FIG. 5.

As shown in FIG. 5, it can be seen that the biodegradable microspheres prepared according to the present invention released a drug in a sustained manner

Test Example 6: Testing of Optimum Solvent Mixing Ratio for Preparation of Single-Phase Mixed Solution Single-phase mixed solutions were prepared in the same manner as in Example 1 of Preparation Example 1 while using methanol as an example of alcohol and varying a mixing ratio of water and methanol and a mixing ratio of the mixture of water and methanol and dichloromethane (DCM; non-polar solvent) as shown in Table 1 to identify optimum solvent mixing ratios, and the mixed solutions were examined to determine whether phase separation had occurred, and results thereof are shown in Table 1.

TABLE 1

| | Water/methanol mixture:DCM | | | | | | | | | | | | |
|---|---|---|---|---|---|---|---|---|---|---|---|---|---|
| Water/Methanol | 1:1 | 1:2 | 1:3 | 1:4 | 1:5 | 1:6 | 1:7 | 1:8 | 1:9 | 1:10 | 1:11 | 1:12 | 1:13 |
| 1:9 | X | X | X | X | X | X | X | X | X | X | X | X | O |
| 1:6 | X | X | X | O | O | O | O | O | O | O | O | O | O |
| 1:4 | X | O | O | O | O | O | O | O | O | O | O | O | O |
| 1:3 | O | O | O | O | O | O | O | O | O | O | O | O | O |

(O: phase separation occurred, X: phase separation did not occur)

As shown in Table 1, it can be seen that in a preparation method of the present invention, an optimum mixing ratio of water and alcohol in a mixture thereof is in the range of 1:4 to 1:9, and that an optimum mixing ratio of the water/alcohol mixture and the non-polar organic solvent (in which a biodegradable polymer is dissolved) is in the range of 1:1 to 1:12.

What is claimed is:

1. A method of preparing biodegradable microspheres having uniform drug loading efficiency, comprising the steps of:
    i) dissolving a drug in a mixed solvent in which water and alcohol are mixed in a volume ratio of 1:4 to 1:9 to form a drug solution;
    ii) adding the drug solution obtained in step i) to a non-polar organic solvent in which a biodegradable polymer is dissolved, thus forming a single-phase mixed solution without forming an emulsion;
    iii) dispersing the single-phase mixed solution in an aqueous phase in which a surfactant is dissolved, thus forming a microsphere emulsion;
    iv) evaporating the non-polar organic solvent in the microsphere emulsion formed in step iii), and then hardening the microspheres; and
    v) obtaining the microsphere powder by a freeze-drying,
    wherein the alcohol is methanol or ethanol,
    wherein the drug is a water-soluble drug,
    wherein the biodegradable polymer is poly(lactic-co-glycolic acid) or poly(lactic acid),
    wherein the non-polar organic solvent is dichloromethane or chloroform, and
    wherein in step ii), the volume ratio at which the drug solution and the non-polar organic solvent in which the biodegradable polymer is dissolved are mixed is in a range of 1:1 to 1:12.

2. The method of claim 1, wherein the surfactant is one or more selected from the group consisting of Polysorbate 20, Polysorbate 60, Polysorbate 80, and polyvinyl alcohol.

3. The method of claim 1, wherein the drug is a peptide.

4. The method of claim 3, wherein the peptide is leuprorelin or a salt thereof.

5. A method of preparing a single-phase mixed solution usable for preparing biodegradable microspheres, comprising the steps of:
    a) dissolving a drug in a mixed solvent in which water and alcohol are mixed in a volume ratio of 1:4 to 1:9 to form a drug solution; and
    b) adding the drug solution obtained in step a) to a non-polar organic solvent in which a biodegradable polymer is dissolved, thus forming a single-phase mixed solution,
    wherein, in step b), the volume ratio at which the drug solution and the non-polar organic solvent in which the biodegradable polymer is dissolved are mixed is in a range of 1:1 to 1:12,
    wherein the alcohol is methanol or ethanol,
    wherein the drug is a water-soluble drug,
    wherein the biodegradable polymer is poly(lactic-co-glycolic acid) or poly(lactic acid),
    wherein the non-polar organic solvent is dichloromethane or chloroform, and
    wherein the single-phase mixed solution is stabilized and does not undergo phase separation.

6. The method of claim 5, wherein the drug is a peptide.

7. The method of claim 6, wherein the peptide is leuprorelin or a salt thereof.

* * * * *